United States Patent [19]

Miller

[11] 4,434,307
[45] Feb. 28, 1984

[54] INHIBITING POLYMERIZATION OF VINYL AROMATIC MONOMERS

[75] Inventor: Richard F. Miller, Humble, Tex.

[73] Assignee: Atlantic Richfield Company, Los Angeles, Calif.

[21] Appl. No.: 453,070

[22] Filed: Dec. 27, 1982

[51] Int. Cl.$^3$ ............................................. C07C 7/18
[52] U.S. Cl. ......................................... 585/4; 585/5; 585/950
[58] Field of Search .............................. 585/4, 5, 950

[56] References Cited

U.S. PATENT DOCUMENTS

| | | | |
|---|---|---|---|
| 2,320,859 | 6/1943 | Foord | 585/5 |
| 2,361,538 | 10/1944 | Franz | 585/5 |
| 2,402,113 | 6/1946 | Hatch et al. | 585/5 |
| 2,809,155 | 10/1957 | Buehler | 585/5 |
| 2,867,672 | 1/1959 | Hemmerick | 585/4 |
| 3,148,225 | 9/1964 | Albert | 585/4 |
| 3,265,752 | 8/1966 | Whiten | 585/4 |
| 3,309,412 | 3/1969 | Sakuragi et al. | 585/5 |
| 3,340,160 | 6/1964 | Waldby | 208/48 A |
| 3,417,154 | 12/1968 | Albert et al. | 585/5 |

FOREIGN PATENT DOCUMENTS 504780  5/1939  United Kingdom .................. 585/4

*Primary Examiner*—Delbert E. Gantz
*Assistant Examiner*—Cynthia A. Prezlick
*Attorney, Agent, or Firm*—Coleman R. Reap

[57] ABSTRACT

Vinyl aromatic compounds are stabilized against undesired polymerization by adding to the vinyl aromatic compounds small amounts of at least one N,N-diarylhydroxylamine and at least one mono-or ditertiary alkyl catechol and/or at least one mono-or ditertiary alkylhydroquinone.

10 Claims, No Drawings

INHIBITING POLYMERIZATION OF VINYL AROMATIC MONOMERS

FIELD OF THE INVENTION

The present invention relates to the stabilization of ethylenically unsaturated compounds and more particularly to the inhibition of undesired polymerization of vinyl aromatic compounds during storage, shipping or processing.

BACKGROUND

Vinyl aromatic compounds such as styrene undergo undesired spontaneous polymerization (i.e. polymerization of monomers due to heat or the random generation of free radicals in the monomers) during storage, shipping or processing. The problem is particularly acute during purification operations carried out at elevated temperatures such as distillation. Spontaneous polymerization is disadvantageous not only because it causes fouling of distillation column reboilers and other equipment used for processing the vinyl aromatic monomer but also because it usually renders the monomer unfit for use without further treatment. Accordingly, it is desirable and often necessary to inhibit the spontaneous polymerization of vinyl aromatic monomers.

PRIOR ART

To prevent spontaneous polymerization of vinyl aromatic monomers it is common practice to add to the monomers compounds which have polymerization inhibiting activity. A wide variety of such compounds, known as polymerization inhibitors, have been used for this purpose. Sulfur has been widely used in the past to inhibit polymerization of vinyl aromatic compounds, however sulfur usage is undesirable because large quantities of sulfur are required for effective polymerization inhibition. This presents a waste removal problem when the monomer is separated from the sulfur-monomer mixture, which is accomplished by distillation. The distillation bottoms product, which contains higher molecular weight hydrocarbons, polymer and sulfur, cannot be burned due to the air pollution hazard caused by sulfur oxides. Thus, this material must be disposed of by burial in a waste dump.

I recent times, many chemical compounds have been developed as substitutes for sulfur in polymerization inhibiting applications. These compounds have been used as polymerization inhibitors for vinyl aromatic monomers with varying degrees of success. U.S. Pat. No. 3,390,198, issued to Leston, discloses the use of several mono and dialkylcatechols as polymerization inhibitors for hot styrene. U.S. Pat. Nos. 4,061,545 and 4,177,110 issued to Watson, discloses the use of a combination of tertiary-butylcatechol and phenothiazine as a polymerization inhibitor system for vinyl aromatic compounds. U.S. Pat. No. 3,148,225, issued to Albert, employs dialkylhydroxylamines for inhibiting popcorn polymers formation in styrene-butadiene rubbers. The dialkylhydroxylamine compounds appear to react with and terminate free radicals which cause undesired formation of polymers. U.S. Pat. No. 2,965,685, issued to Campbell, discloses inhibiting polymerization by adding about 5 ppm to 5 percent dialkylhydroxyamine to styrene monomer. Sato et al, in U.S. Pat. No. 3,849,498, teach the use of diethylhydroxylamine as a polymerization inhibitor for an alcoholic solution of unsaturated aldehydes. MayerMader et al, U.S. Pat. No. 3,878,181, employ diethylhydroxylamine either alone or in combination with a water soluble amine such as triethanolamine to terminate the aqueous emulsion polymerization of chloroprene. U.S. Pat. No. 3,426,063 discloses the use of N-nitrosoaralkylhydroxylamines to inhibit thermal polymerization of ethylenically unsaturated hydrocarbons.

It has now been discovered that mixtures of N,N-arylhydroxylamines and mono- and di tertiary alkyl pyrocatechols, commonly referred to as mono- and di tertiary alkylcatechols, and/or mono- and di tertiary alkylhydroquinones provide outstanding polymerization inhibiting activity for vinyl aromatic monomers. Thus, because of the synergistic effect of these mixtures it is now possible to provide unexpectedly superior polymerization inhibiting protection with the same total equivalent weight of N,N-diarylhydroxylamines and mono- and di tertiary alkylcatechol or mono- and di tertiary alkylhydroquinone mixtures than is obtainable by the use of members of either of these groups of compounds by themselves.

Accordingly, it is object of the invention to present stable compositions of vinyl aromatic monomers. It is another object of the invention to present a method of effectively and economically inhibiting spontaneous polymerization of styrene and other vinyl aromatic monomers. These and other objects of the invention are set forth in the following description and examples of the invention.

SUMMARY OF THE INVENTION

According to the invention the protection of vinyl aromatic monomers against spontaneous polymerization is accomplished by incorporating into the monomers a polymerization inhibiting system comprised of at least one aromatic disubstituted hydroxylamine and one or more mono- or di tertiary alkylcatechols and/or mono- or di tertiary alkylhydroquinones each tertiary alkyl group of which has 4 to 20 carbon atoms.

DETAILED DESCRIPTION OF THE INVENTION

The term vinyl aromatic monomer as used in this description includes any of the readily polymerizable vinyl aromatic compounds, e.g. styrene, alpha alkyl styrene, such as alpha methyl styrene, ring alkyl substituted styrene such as p-methyl styrene, diethylenically substituted benzene compounds, such as divinylbenzene, etc. and mixtures thereof.

The N,N-diarylhydroxylamine compounds used in the invention have the structural formula RRNOH wherein R and R' are the same or different aromatic hydrocarbon radicals having the structural formula

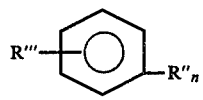

wherein R" is a straight- or branched-chain alkylene radical having 1 to 10 carbon atoms, R''' is hydrogen or a straight- or branched-chain alkyl group having 1 to 6 carbon atoms and n is 0 or 1. In preferred embodiments R and R' are phenyl or aromatic radicals as described above wherein R" has 1 to 6 carbon atoms and R'" is hydrogen. When n is 0, R" does not exist and the phenylene group is attached to the nitrogen atom. Although, N,N-diaromatic-substituted hydroxylamines having more than the above specified number of alkyl or alkylene carbon atoms in each aromatic substituent group may be useful in the invention it is preferred that compounds containing the above-stated upper limits be used in the invention because the latter compounds provide completely satisfactory results and they are easier to prepare. Mixtures of two or more of such diaromatic substituted hydoxylamines can also be advantageously used in the compositions of the invention.

Suitable diaromatic substituted hydroxylamines include N,N-diphenylhydroxylamine, N,N-dibenzylhydroxylamine N-phynyl-N-(3-phenylpropyl)hydroxylamine, N,N-bis (2-methyl-8-phenyloctyl)hydroxylamine, N,N-bis[4-(1,1-dimethylethyl)phenyl]hydroxylamine, N,N-bis(3-hexylphenyl-4-butyl)hydroxylamine, N-phenyl-N-(4-ethylphenyl-2-ethyl)hydroxylamine, etc. Preferred diaromatic substituted hydroxylamines include N,N-diphenylhydroxylamine, N,N-dibenzylhydroxylamine, N,N-bis(3-phenylpropyl)hydroxylamine, etc. As noted above, two or more of these compounds may be used in combination, if desired.

Tertiary mono- and di alkylcatechol compounds useful in the invention are those having the structural formula

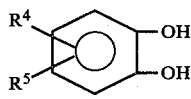

wherein $R^4$ is a tertiary alkyl group having a total of 4 to 20 or more carbon atoms and $R^5$ is hydrogen or a tertiary alkyl group having a total of 4 to 20 or more carbon atoms. The number of alkyl carbon atoms in each of $R^4$ and $R^5$ may exceed 20 but no particular advantage is derived from the use of such high molecular weight compounds. The tertiary alkyl groups may be straight or branched-chain. Preferred mono- and di tertiary alkylcatechols are those in which the total number of alkyl carbon atoms in each of $R^4$ and $R^5$ (where $R^5$ is not hydrogen) is not more than 10, i.e. the preferred total number is 4 to 10. Mixtures of two or more mono- and/or di tertiary alkylcatechols of the above description may be used in the invention if desired.

Suitable mono- and di tertiary alkylcatechols include 4-(t-butyl)catechol, 3-(1,1-diethylethyl)catechol, 4-(1-ethyl-1-methyl hexyl)catechol, 3-(1,1-diethylpropyl)-catechol, 4-tributylmethylcatechol, 4-trihexylmethylcatechol, 3,4-bis(t-butyl)catechol, 3-t-butyl-4(1,1-diethylethyl)catechol, 3,4-bis(tributylmethyl)catechol, etc. Preferred mono- and di tertiary alkylcatechols include 4-(t-butyl)catechol, 4-(1,1-diethylethyl)catechol, 3,4-bis(t-butyl)catechol, etc.

Mono- and di tertiary alkylhydroquinones useful in the invention are those having the structural formula

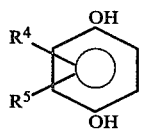

wherein $R^4$ and $R^5$ are as defined above. The preferred mono- and di tertiary alkylhydroquinones are those in which the total number of carbon atoms in each of $R^4$ and $R^5$ (when $R^5$ is not hydrogen) is not more than 10, i.e. the preferred total number is 4 to 10. Mixtures of two or more mono- and di tertiary alkylhydroquinones may be used in the invention.

Suitable mono- and di tertiary alkylhydroquinones include t-butylhydroquinone, 1,1-diethylethylhydroquinone, triethylmethylhydroquinone, tripropylmethylhydroquinone, 2,3-bis(t-butyl)hydroquinone, 2,5-bis(t-butyl)hydroquinone, 2-t-butyl-3(1,1-diethylethyl)hydroquinone, 2,6-bis(tributylmethyl)hydroquinone, etc. Preferred mono- and di tertiary alkylhydroquinones include 2-(t-butyl)hydroquinone, 2-(1,1-diethyl)hydroquinone, 2,3-bis(t-butyl)hydroquinone, 2,5-bis(t-butyl)hydroquinone, 2-t-butyl-3(1,1-diethylethyl)hydroquinone 2,6-bis(tributylmethyl)hydroquinone, etc.

In some cases it may be desirable to use mixtures of one or more mono- and di tertiary alkylcatechols and one or more mono- and di tertiary alkylhydroquinones. Such mixtures are also within the scope of the invention.

Some N,N-diarylhydroxylamines, such as N,N-dibenzlhydroxylamine and mono- and di tertiary alkylhydroquinones, and some mono- and di tertiary-alkylcatechols, such as 4-tertiary-butyl catechol, are available commercially. Those N,N-diarylhydroxylamines, mono- and di tertiary-alkylcatechols and mono- and di tertiary alkylhydroquinones which are not commercially avaialable may be prepared by any of the well known techniques. The preparation of these compounds forms no part of the present invention.

The relative concentrations of N,N-diarylhydroxylamine and total mono- and di tertiary alkylcatechol and/or mono- and di tertiary alkylhydroquinone used in the invention are generally in the range of about 10 to 90 weight percent N,N-diarylhydroxylamine and 90 to 10 weight percent total mono- and di tertiary-alkylcatechol and/or mono- and di tertiary alkylhydroquinone, based on the total combined weight of these components. In preferred embodiments the concentrations generally fall in the range of about 25 to 75 weight percent N,N-diarylhydroxylamine and 75–25% total mono- and di tertiary alkylcatechol and/or mono- and di tertiary alkylhydroquinone, based on the total combined weight of these components.

The polymerization inhibiting system of the invention is particularly well suited for protecting the reboiler sections of a distillation column during distillation of vinyl aromatic monomers because of the high boiling point of the inhibitor compounds in the system. The inhibitor system may be used at temperatures up to about 400° C. or higher at atmospheric pressure. Since the boiling point of various members of each of the two classes of compounds, i.e. diarylhydroxylamines and mono- and di tertiary alkylcatechols mono- and di tertiary alkylhydroquinones, are different, compounds which have the desired boiling point can be easily selected from each class. To make up for the inhibitor which is left behind during distillation, additional ihibitor can be added to the vinyl aromatic monomer after it is distilled from heavier hydrocarbons. In some cases it may be desirable to use lower boiling polymerization inhibitors in combination with the inhibitor system of the invention. For example, when distilling a vinyl aromatic monomer from higher boiling hydrocarbons it may be advantageous to add a polymerization inhibitor which has a boiling point near or lower than the boiling point of the vinyl aromatic compound. This will provide protection to the overhead portion of the column. It may also be desirable to add with the polymerization inhibiting system of the invention other agents, such as corrosion inhibitors, to provide additional protection to process equipment.

The inhibitor system of the invention can be introduced into the monomer to be protected by any conventional method. It is generally introduced just upstream of the point of desired application by any suitable means, such as by the use of a proportionating pump. It can be added to the monomer as a single composition containing all of the desired inhibitor compounds, or the individual components can be added separately or in any other desired combination. The composition may be added as a concentrate, if desired, but it is preferable to add it as a solution which is compatible with the monomer being treated. Suitable solvents include kerosene, naphtha, the lower alkanes such as hexane, aromatic solvents, such as toluene, alcohols, polyols or ketone, etc. It is often preferred to dissolve the inhibitors of the invention in the monomer to which the inhibitor is being added to avoid introducing additional impurities to the monomer. The concentration of inhibitor system in the solvent is desirably in the range of about 1 to 30 weight percent and preferably about 5 to 20 weight percent based on the total weight of inhibitor and solvent.

The polymerization inhibitor system is used at a concentration which is effective to provide the desired protection against spontaneous polymerization. It has been determined that amounts of inhibitor in the range of about 0.5 to 1000 ppm based on the weight of the monomer being treated affords ample protection against undesired polymerization. For most applications the inhibitor system is used in amounts in the range of about 5 to 500 ppm.

The components of the polymerization inhibiting system can be easily removed from the vinyl aromatic monomer prior to polymerization by caustic washing. Such procedures are well known and commonly practiced to separate phenolic type inhibitors, such as tertiary butylcatechol, from monomers.

The following examples will serve to further illustrate the invention. Unless otherwise stated, parts and percentages are on a weight basis. In the examples styrene, which is representative of vinyl aromatic monomers, was used as the test monomer. In the tests sodium ion, in the form of sodium hydroxide, and benzoyl peroxide were added to the test samples to provide a more intensive test of the ability of the inhibitor compositions of the invention to inhibit spontaneous polymerization. Sodium ions and benzoyl peroxide are both known addition polymerization catalysts for vinyl aromatic monomers.

EXAMPLE I (Control)

To distilled styrene was added sufficient sodium hydroxide (as a 50% aqueous solution) to produce a mixture containing 17 mg of sodium hydroxide per each 1000 grams of styrene monomer. This concentration of sodium hydroxide in the monomer is equivalent to a sodium ion concentration of 10 ppm. One hundred grams of the styrene monomer mixture was introduced into a 250 ml Erlenmeyer flask fitted with a ground glass stopper. Two hundred ppm, based on the weight of styrene, of benzoyl peroxide was added to the flask and the flask was then purged of air by bubbling nitrogen gas through the monomer. After the nitrogen purge the ground glass stopper was inserted into the flask and the flask was placed in an oven. The temperature of the oven was raised to and maintained at a temperature of $90° \pm 2°$ C. for the duration of the test. A ten ml sample was drawn from the flask after 120 minutes.

The sample was tested to determine the amount of styrene polymer formed by the following procedure: The 10 ml sample of styrene monomer was introduced into 100 ml of cold methanol, quenching the polymerization reaction. The methanol-monomer mixture was heated sufficiently to coagulate the polymer formed. The polymer was recovered from the methanol by filtration, dried overnight at a temperature of 100° F. and weighed. The percentage of polymer formed was determined and reported in the Table in the Run 1 row.

EXAMPLE II (Comparative)

The procedure and test of Example I were repeated except that 500 ppm of 4,6-dinitro-o-cresol was added to the Erlenmeyer flask just prior to the initial nitrogen purge. The styrene monomer was tested for polymer formation as indicated in Example I. The results are tabulated in the Table in the Run 2 row.

EXAMPLE III (Comparative)

The procedure and test of Example II were repeated except that 250 and 500 ppm of dibenzylhydroxylamine were substituted for the 4,6-dinitro-o-cresol. The results are tabulated in the Table in the Run 3 rows.

EXAMPLE IV

The procedure and tests of Example II were repeated except that 150 and 250 ppm of 4-t-butylcatechol were substituted for the 4,6-dinitro-o-cresol. The results are tabulated in the Table in the Run 4 rows.

EXAMPLE V (Comparative)

The procedure and test of Example II were repeated except that 500 ppm of 2,5-di-t-butylhydroquinone was substituted for the 4,6-dinitro-o-cresol. The result is tabulated in the Table in the Run 5 row.

EXAMPLE VI

The procedure and tests of Example II were repeated except that the 4,6-dinitro-o-cresol was replaced by various amounts of a 50:50 weight percent blend of dibenzylhydroxylamine and 2,5-di-t-butylhydroquinone. The results are tabulated in the Table in the Run 6 rows.

EXAMPLE VII

The procedures and tests of Example II were repeated except that the 4,6-dinitro-o-cresol was replaced by various amounts of 50:50 weight percent blend of dibenzylhydroxylamine and 4-t-butylhydroquinone. The results were tabulated in the Table in the Run 7 rows.

TABLE

Time Min. 120

| Run | Inhibitor | Inhibitor Concentration, ppm | Weight % Polymer Formed After 120 Minutes |
|---|---|---|---|
| 1 | None | — | * |
| 2 | 4,6-dinitro-o-cresol | 500 | 1.17 |
| 3 | dibenzylhydroxylamine | 250 | 10.70 |
|   |   | 500 | 8.30 |
| 4 | 4-t-butylcatechol | 150 | 4.32 |
|   |   | 250 | 3.35 |
| 5 | 2,5-di-t-butylhydroquinone | 500 | 1.94 |
| 6 | dibenzylhydroxylamine/ 2,5-di-t-butylhydroquinone (50:50 weight % blend) | 100 | 6.39 |
|   |   | 200 | 2.72 |
|   |   | 300 | 0.92 |
|   |   | 400 | 0.30 |
|   |   | 500 | 0.01 |
| 7 | dibenzylhydroxylamine/ 4-t-butylcatechol (50:50 weight % blend) | 150 | 2.55 |
|   |   | 250 | 1.51 |
|   |   | 500 | 0.08 |

*the polymer was too viscous to remove from test vessel with a pipette

The benefit of the use of the polymerization inhibitor compositions of the invention are shown in the Table. In the Table was uninhibited monomer was so viscous due to polymer formation after two hours that a sample could not be drawn; the Run 2 monomer sample, which was inhibited by a widely used styrene polymerization inhibitor, 4,6-dinitro-o-cresol, contained 1.17 polymer at the end of the two hour period; the two hour anlysis of the Runs 3, 4 and 5 samples, which each contained one of the components of the inhibitor system of the invention, showed considerable polymer concentrations; the two hour analyses of the Run 6 and 7 samples which each contained one inhibitor composition of the invention showed very low polymer concentrations. Thus, one inhibitor system of the invention (Run 6) used at 500 ppm shows a greater than 100-fold improvement over the use of the next most effective prior art inhibitor, 4,6-dinitro-o-cresol, at the same concentration. Another inhibitor system of the invention (Run 7) showed a greater than 14-fold improvement over the 4,6-dinitro-o-cresol at the same concentration.

Although the invention is described with particular reference to specific examples, it is understood that the invention includes obvious variants. For example, diaryl hydroxylamines other than dibenzylhydroxylamine can be used in the invention and the inhibitor system can be formulated to contain more than one member from each of the specified classes of compounds. The scope of the invention is limited only by the breadth of the appended claims.

What is claimed is:

1. A composition comprised of a vinyl aromatic compound and an amount effective to inhibit polymerization of said vinyl aromatic compound of
   (1) at least one hydroxylamine containing two N-substituted hydrocarbon groups each of which contains an aromatic radical, and
   (2) at least one mono- or ditertiary alkyl dihydroxybenzene compound selected from mono- and ditertiary alkylcatechols and mono- and ditertiary alkylhydroquinones.

2. A composition comprised of a vinyl aromatic compound containing an amount effective to inhibit polymerization of said vinyl aromatic compound of a mixture of
   (1) at least one compound having the structural formula

RR'NOH wherein R and R' are the same or different hydrocarbon radicals having the structural formula

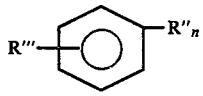

wherein R" is an alkylene radical having 1 to 10 carbon atoms, R''' is hydrogen or an alkyl group having 1 to 6 carbon atoms and n is 0 or 1,
   (2) at least one compound having the structural formula

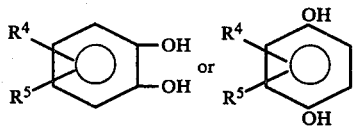

wherein $R^4$ is a tertiary alkyl group having a total of 4 to 20 carbon atoms and $R^5$ is hydrogen or a tertiary alkyl group having a total of 4 to 20 carbon atoms.

3. The composition of claim 2 wherein the total concentration of the compounds in (1) and (2) in said composition is 0.5 to 1000 ppm, based on the total weight of vinyl aromatic compound and the relative concentration of the compounds in (1) and (2) are 90 to 10 parts by weight and 10 to 90 parts by weight respectively.

4. The composition of claim 2 wherein the vinyl aromatic compound is styrene or alkyl-substituted styrene, R" has 1 to 6 carbon atoms, the tertiary alkyl groups in (2) have 4 to 8 carbon atoms, the relative concentrations of the compounds in (1) and (2) are 25 to 75 parts by weight and 75 and 25 parts by weight respectively and the total concentration of the compounds in (1) and (2) in said composition is 5 to 500 ppm, based on total weight of vinyl aromatic compound.

5. The composition of claim 4 wherein the vinyl aromatic compound is styrene, the compound in (1) is N,N-dibenzlhydroxylamine and the compound in (2) is selected from mono- and ditertiary butylcatechols, mono- and ditertiary butylhydroquinones and mixtures of these.

6. In a method of inhibiting polymerization of a vinyl aromatic compound comprising adding to the vinyl aromatic compound an amount of a polymerization inhibiting agent effective to substantially reduce the rate of polymerization, the improvement comprising using as the agent a mixture comprised of:
   (1) at least one hydroxylamine containing two N-substituted hydrocarbon groups each of which contains an aromatic radical, and
   (2) at least one mono- or ditertiary alkyl dihydroxybenzene compound selected from mono- and ditertiary alkylcatechols and mono- and ditertiary alkylhydroquinones.

7. In a method of inhibiting polymerization of a vinyl aromatic compound comprising adding to the vinyl aromatic compound an amount of a polymerization inhibiting agent effective to substantially reduce the rate of polymerization, the improvement comprising using as the agent a mixture of:

(1) at least one compound having the structural formula

RR'NOH wherein R and R' are the same or different hydrocarbon radicals having the structural formula

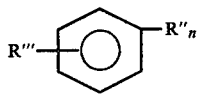

wherein R'' is an alkylene radical having 1 to 10 carbon atoms, R''' is hydrogen or an alkyl group having 1 to 6 carbon atoms and n is 0 or 1, and (2) at least one compound having the structural formula

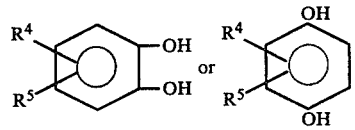

wherein $R^4$ is a tertiary alkyl group having a total of 4 to 20 carbon atoms and $R^5$ is hydrogen or a tertiary alkyl group having a total of 4 to 20 carbon atoms.

8. The process of claim 7 wherein the total concentration of the compounds in (1) and (2) in said composition is 0.5 to 1000 ppm, based on the total weight of vinyl aromatic compound and the relative concentration of the compounds in (1) and (2) are 90 to 10 parts by weight and 10 to 90 parts by weight respectively.

9. The process of claim 7 wherein the vinyl aromatic compound is styrene or alkyl-substituted styrene, R'' has 1 to 6 carbon atoms, the tertiary alkyl groups in (2) have 4 to 8 carbon atoms, the relative concentrations of the compounds in (1) and (2) are 25 to 75 parts by weight and 75 to 25 parts by weight respectively and the total concentration of the compounds in (1) and (2) in said composition is 5 to 500 ppm, based on total weight of vinyl aromatic compound.

10. The process of claim 9 wherein the vinyl aromatic compound is styrene, the compound in (1) is N,N-dibenzlhydroxylamine and the compound in (2) is selected from mono- and ditertiary butylcatechol, mono- and ditertiary butylhydroquinones and mixtures of these.

* * * * *

UNITED STATES PATENT AND TRADEMARK OFFICE
CERTIFICATE OF CORRECTION

PATENT NO. : 4,434,307

DATED : February 28, 1984

INVENTOR(S) : Richard F. Miller

It is certified that error appears in the above-identified patent and that said Letters Patent are hereby corrected as shown below:

Column 8, line 42 change "75 and 25" to -- 75 to 25 --

Signed and Sealed this

Sixteenth Day of October 1984

[SEAL]

Attest:

GERALD J. MOSSINGHOFF

Attesting Officer

Commissioner of Patents and Trademarks